United States Patent
Wang et al.

(10) Patent No.: US 9,137,784 B2
(45) Date of Patent: Sep. 15, 2015

(54) RESOURCE DISTRIBUTION METHOD FOR THROUGHPUT MAXIMIZATION IN COOPERATIVE COGNITIVE SIMO NETWORK

(75) Inventors: Jinlong Wang, Jiangsu (CN); Qihui Wu, Jiangsu (CN); Yang Yang, Jiangsu (CN); Yuming Zhang, Jiangsu (CN)

(73) Assignee: PLA UNIVERSITY OF SCIENCE AND TECHNOLOGY, Baixia Nanjing, Jiangsu (CN)

( * ) Notice: Subject to any disclaimer, the term of this patent is extended or adjusted under 35 U.S.C. 154(b) by 292 days.

(21) Appl. No.: 13/520,175

(22) PCT Filed: Jun. 30, 2011

(86) PCT No.: PCT/CN2011/076732
§ 371 (c)(1),
(2), (4) Date: Nov. 19, 2012

(87) PCT Pub. No.: WO2013/000169
PCT Pub. Date: Jan. 3, 2013

(65) Prior Publication Data
US 2013/0059615 A1    Mar. 7, 2013

(30) Foreign Application Priority Data

Jun. 29, 2011  (CN) .......................... 2011 1 0180262

(51) Int. Cl.
*H04W 72/00*  (2009.01)
*H04W 72/04*  (2009.01)
*H04W 16/10*  (2009.01)
*C07F 15/00*  (2006.01)

(52) U.S. Cl.
CPC ........... *H04W 72/04* (2013.01); *C07F 15/0033* (2013.01); *H04W 16/10* (2013.01)

(58) Field of Classification Search
CPC ..... H04W 72/04; H04W 76/02; H04W 16/10; H04W 16/14
USPC ......................... 455/450–453, 509
See application file for complete search history.

(56) References Cited

U.S. PATENT DOCUMENTS

2013/0065511 A1* 3/2013 Wu et al. ........................... 455/7

* cited by examiner

*Primary Examiner* — Raymond Dean
(74) *Attorney, Agent, or Firm* — Tianhua Gu; Global IP Services

(57) ABSTRACT

A resource distribution method for throughput maximization in a cooperative cognitive SIMO network. The primary user sends data after receiving a cooperation confirmation message, and the cognitive network keeps silent, receives the information data of the primary user and simultaneously decodes the data. The cognitive users which successfully decode the data send the data of themselves to the cognitive base station and forward the data of the primary user; the cognitive users which cannot successfully decode the data only send the data of themselves and do not forward the data of the primary user. The cognitive base station eliminates the interference of the data of primary user and performs beamforming for the signals. According to the combined adjustment the maximum throughput performance can be realized in the cognitive network.

6 Claims, 3 Drawing Sheets

(a)

(b)

RESOURCE DISTRIBUTION METHOD FOR THROUGHPUT MAXIMIZATION IN COOPERATIVE COGNITIVE SIMO NETWORK

CROSS REFERENCE TO RELATED PATENT APPLICATION

The present application is the US national stage of PCT/CN2011/076732 filed on Jun. 30, 2011, which claims the priority of the Chinese patent application No. 201110180262.7 filed on Jun. 29, 2011, which application is incorporated herein by reference.

FIELD OF THE INVENTION

The invention belongs to the technical field of cognitive radio and specifically relates to a new resource distribution method for throughput maximization in a cooperative relay-based cognitive single-input multiple-output (referred to as SIMO) network.

BACKGROUND OF THE INVENTION

Cognitive radio is one of the most popular wireless techniques. The emergence of the cognitive radio has changed the way of exclusively using spectrum resources by a licensed user. Each cognitive user can perform interactive perception with the wireless communication environment and automatically changes its transmit-receive parameters, so that the authorized spectrum can be dynamically reused on the premise of ensuring the normal communication of the licensed user (primary user) and the utilization efficiency of the spectrum can be significantly improved. In addition, a multi-antenna way is recognized as one of the required technical schemes for further high-speed wireless networks. A multi-antenna communication system increases space dimension on the basis of original frequency domain, time domain and code domain, with the advanced space-time signal processing technologies, its capacity can be upgraded by many times without increasing bandwidth and transmission power, in addition, the anti-interference and anti-fading performances of the communication system can be simultaneously enhanced, so that the scarce spectrum can be effectively eased and high-speed business development can be further provided. The combination of the multi-antenna technique and the cognitive radio technique can be combined to realize broad application.

At present, there are two well-known spectrum access models for cognitive radio, namely the spectrum hole-based opportunistic spectrum access and the interference temperature-based spectrum sharing.

The spectrum hole-based opportunistic spectrum access is as follows: spectrum resources which are not used by the primary user in specific positions at specific times are called as spectrum holes, and the opportunistic spectrum access manner utilizes the spectrum holes to communicate, which is the direct realization of cognitive radio. This kind of access way does not need to control the transmission power, but a high-precision spectrum detection technique is required in the cognitive network; and when the traffic in primary network is busy, it is very difficulty to obtain the communication opportunity in the opportunistic spectrum access model.

The interference temperature-based spectrum sharing is as follows: interference temperature is defined at the front end of radio frequency of a wireless receiver, which is used for measuring the interference received by a receiver in a certain geographical position within a certain frequency band, and the maximum interference temperature which can be tolerated by normal communication of the receiver is called as an interference temperature boundary. As long as the interference from the cognitive network to the primary receiver can be controlled within the interference temperature boundary, the licensed frequency band can be reused by the cognitive user without affecting the normal communication of the primary user. By utilizing this kind of access way, the cognitive network and the primary user can simultaneously use the same licensed frequency band in the same position, but the transmission power of the cognitive network must be controlled to meet the interference temperature boundary of the primary user, so that the spectrum sharing way can not realize a large-range network coverage and the communication performance is very poor when the distance to the primary network is short.

At present, in order to overcome the problems of difficult access and poor communication in the existing cognitive radio access methods, the applicant provides an application number of CN201110178680.2 named "Cognitive SIMO Network Access Method Based on Cooperative Relay", which proposes a new access method for the uplink of a multi-antenna cognitive network. The access method allows the cognitive network and the primary user to simultaneously use the same licensed spectrum in the same geographical position, furthermore, a large-range network coverage can be realized and great network throughput can be obtained when the distance to the primary network is short, which overcomes the deficiencies in the existing cognitive radio access methods. However, for the access method, how to realize high-efficient resource distribution, to maximize the throughput of the cognitive SIMO network on the premise of ensuring the target transmission rate of the primary user is a problem needed to be solved urgently.

SUMMARY OF THE INVENTION

The invention aims to provide a resource distribution method for throughput maximization in cooperative cognitive SIMO network on the premise of ensuring the target transmission rate of a primary user.

The invention is realized through the following technical scheme:

A resource distribution method for throughput maximization in a cooperative cognitive SIMO network comprises the following steps:

Step 1: the transmitter of the primary user broadcasts a cooperation request message (referred to as CRM), the receiver of the primary user replies a cooperation acknowledge message (referred to as CAM). The cognitive base station estimates the channel state information in the network from the received CRM and CAM, then judges whether the cognitive SIMO network has the ability of cooperating with the primary user to achieve the target transmission rate of the primary user or not, if yes, the cognitive base station sends a cooperation confirmation message (referred to as CCM) to the primary user and the cognitive SIMO network is accessible to the frequency band licensed to the primary user; and if no, the cognitive SIMO network is non-accessible to the licensed frequency band;

Step 2: the cognitive network receives the data of the primary user, that comprises:

after the transmitter and the receiver of the primary user receive the CCM, the transmitter of the primary user starts to send the information data, the cognitive network keeps silent and receives data of the primary user, simultaneously, the cognitive base station and the cognitive users being capable of successfully decoding the data of the primary user decode the data;

Step 3: the cognitive users send data of themselves and simultaneously relay the data of the primary user, that comprises:

the cognitive users which successfully decode the data of the primary user use part of their transmission power $\alpha_c p_c$, $c \in U_1$ to send the data of themselves to the cognitive base station, and the remaining transmission power $(1-\alpha_c)p_c$, $c \in U_1$ is used for forwarding the data of the primary user to the primary receiver; the cognitive users which can not successfully decode the data do not forward the data of the primary user, all their transmission power $p_c$, $c \in U_2$ is used for sending the data of themselves to the cognitive base station, Wherein the set $U_1$ represents the set of the cognitive users being capable of successfully decoding the data of the primary user, the set $U_2$ represents the set of the cognitive users being incapable of successfully decoding the data of the primary user, $p_c$ represents the transmission power of the cth cognitive user and $\alpha_c$ represents the power distribution factor of the cth cognitive user;

Step 4: the cognitive base station eliminates the interference caused by the data of the primary user from the received mixed signals and performs beamforming for the signals after eliminating the interference. According to the combined adjustment of the transmission power vector $p=[p_1, p_2, \ldots, p_N]^T$, the power distribution factor vector $\alpha=[\alpha_1, \alpha_2, \ldots, \alpha_N]^T$, $\alpha_c=1$, $c \in U_2$, and the beamforming weight vectors $w_c=[w_{c,1}, w_{c,2}, \ldots, w_{c,M}]^T$, $c=1, 2, \ldots, N$, the maximum throughput can be realized in the cognitive SIMO network on the premise of ensuring the target transmission rate of the primary user. Wherein M represents the number of antennas configured at the cognitive base station, and N represents the number of the cognitive users in the cognitive network.

The specific implementation method of the step 4 in the invention is as follows:

4.1 Initializing: $n=0$, $p_c^{(n)}=p_{c,max}$, $c=1, 2, \ldots, N$, $\alpha_c^{(n)}=x$, $c=1, 2, \ldots, N$ and $R_{sum}^{(n)}=0$, wherein n represents the number of iterations, $p_c^{(n)}$ and $\alpha_c^{(n)}$ represent the transmission power and the power distribution factor of the cth cognitive user at the nth iteration respectively, $p_{c,max}$ represents the peak transmission power allowed by the cth cognitive user, and $R_{sum}^{(n)}$ represents the throughput of the cognitive network at the nth iteration; and setting a judging criterion of iteration stopping $\epsilon$, $\epsilon \in [10^{-2}, 10^{-4}]$;

4.2 Adding 1 to the number of the iterations: $n=n+1$;

4.3 Fixing the transmission power vector and the power distribution factor vector as $p^{(n-1)}$ and $\alpha^{(n-1)}$ of the (n−1)th iteration, and enabling the cognitive base station to utilize a maximum SINR beamforming criterion to calculate the beamforming weight vectors $w_c^{(n)}$, $c=1, 2, \ldots, N$ of the nth iteration, wherein the calculation formula is as follows:

$$w_c^{(n)} = \eta \left( \sum_{i=1, i \neq c}^{N} \alpha_i^{(n-1)} p_i^{(n-1)} h_i^{cbH} h_i^{cb} + \sigma_b^2 I_M \right)^{-1} h_c^{cb} \quad (1)$$

Wherein $I_M$ represents an M×M unit matrix, $\eta$ is a scaler factor for normalizing $w_c^{(n)}$, and $h_c^{cb}$, $c=1, 2, \ldots, N$ represents an M-dimensional channel vector response from the cth cognitive user to the cognitive base station, $h_i^{cbH}$ is a conjugate of $h_i^{cb}$, and $\sigma_b^2$ represents the channel noise power received by the cognitive base station;

4.4 Fixing the beamforming weight vectors as $w_c^{(n)}$, $c=1, 2, \ldots, N$ of the nth iteration, fixing the power distribution factor vector as $\alpha^{(n-1)}$ of the (n−1)th iteration and calculating the transmission power vector $p^{(n)}$ of the nth iteration;

4.5 Fixing the beamforming weight vectors and the transmission power vector as $w_c^{(n)}$, $c=1, 2, \ldots, N$ and $p^{(n)}$ of the nth iteration and calculating the power distribution factor vector $\alpha^{(n)}$ of the nth iteration;

4.6 Calculating the throughput $R_{sum}^{(n)}$ of the cognitive network after the nth iteration by utilizing the following formula:

$$R_{sum}^{(n)} = \sum_{c=1}^{N} \frac{1}{2} \log \left( 1 + \frac{\alpha_c^{(n)} p_c^{(n)} |w_c^{(n)H} h_c^{cb}|^2}{\sum_{i=1, i \neq c}^{N} \alpha_i^{(n)} p_i^{(n)} |w_c^{(n)H} h_i^{cb}|^2 + \sigma_b^2} \right) \quad (2)$$

4.7 Judging whether the iteration stopping condition $|R_{sum}^{(n)} - R_{sum}^{(n-1)}|/R_{sum}^{(n-1)} \leq \epsilon$ is met or not, if so, indicating that the throughputs of the cognitive network, which are obtained in the nth iteration and the (n−1)th iteration hardly change, namely the iteration process converges, then continuously implementing the step 4.8; and otherwise, repeatedly implementing the step 4.2;

4.8 Outputting the final values after convergence: $w_c = w_c^{(n)}$, $c=1, 2, \ldots, N$, $p = p^{(n)}$, $\alpha = \alpha^{(n)}$ and $R_{sum} = R_{sum}^{(n)}$, wherein the throughput $R_{sum}$ of the cognitive network is maximum at this time.

At the nth iteration, the calculation process of the transmission power vector $p^{(n)}$ in the step 4.4 is as follows:

1) Initializing: $m=0$ and $\hat{p}_c^{(m)}=0$, $c=1, 2, \ldots, N$, wherein m represents the number of iterations, $\hat{p}_c^{(m)}$ represents the transmission power of the cth cognitive user at the mth iteration, and setting the judging criteria of iteration stopping $\epsilon$, $\epsilon \in [10^{-2}, 10^{-4}]$;

2) Adding 1 to the number of iterations: $m=m+1$;

3) Calculating the transmission power $\hat{p}_c^{(m)}$, $c=1, 2, \ldots, N$ of the cth cognitive user at the mth iteration by utilizing the following formula;

$$\hat{p}_c^{(m)} = \left[ \left( \sum_{k=1, k \neq c}^{N} \frac{\alpha_c^{(n-1)} |w_k^{(n)H} h_c^{cb}|^2}{\sum_{i=1, i \neq k}^{N} \hat{p}_i^{(m-1)} \alpha_i^{(n-1)} |w_k^{(n)H} h_c^{cb}|^2 + \sigma_b^2} \right)^{-1} \right]^{p_{c,max}} \quad (3)$$

Wherein $[b]^{p_{c,max}}$ takes a minimum value of b and $p_{c,max}$;

4) Judging whether the iteration stopping condition $\|\hat{p}^{(m)} - \hat{p}^{(m-1)}\|/\|\hat{p}^{(m-1)}\| \leq \epsilon$ is met or not, if so, indicating that the power vectors obtained in the nth iteration and the (n−1)th iteration hardly change, namely the iteration process converges, then continuously implementing the step 5); and otherwise, repeatedly implementing the step 2);

5) Outputting the final convergent value: $p^{(n)} = \hat{p}^{(m)}$.

At the nth iteration, the calculation process of the power distribution factor vector $\alpha^{(n)}$ in the step 4.5 is as follows:

1) Initializing: $m=0$, $\hat{\alpha}_c^{(m)}=0$ ($c \in U_1$) and $\hat{\alpha}_c^{(m)}=1$ ($c \in U_2$), wherein m represents the number of iterations, $\hat{\alpha}_c^{(m)}$ represents the power distribution factor of the cth cognitive user at the mth iteration; and setting the judging criteria of iteration stopping $\epsilon$, $\epsilon \in [10^{-2}, 10^{-4}]$;

2) Adding 1 to the number of iterations: m=m+1;
3) Calculating the power distribution factor of the $c(c \in U_1)$ th cognitive user at the mth iteration by utilizing the following formula:

$$\hat{\alpha}_c^{(m)} = \left[\left(\sum_{k \in U_1, k \neq c} \frac{p_c^{(n)}|w_k^{(n)H} h_c^{cb}|^2}{\sum_{i \in U_1, i \neq k} \hat{\alpha}_i^{(m-1)} p_i^{(n)}|w_k^{(n)H} h_i^{cb}|^2 + q_k^1} + \right.\right. \quad (4)$$

$$\left.\left. \sum_{k \in U_2} \frac{p_c^{(n)}|w_k^{(n)H} h_c^{cb}|^2}{\sum_{i \in U_1} \alpha_i^{(m-1)} \bar{p}_i |w_k^{(n)H} h_i^{cb}|^2 + q_k^2} + \lambda g_c(p_c^{(n)})\right)^{-1}\right]^1$$

Wherein $$q_k^1 = \sum_{i \in U_2} p_i^{(n)}|w_k^{(n)H} h_i^{cb}|^2 + \sigma_b^2 (k \in U_1),$$

$$q_k^2 = \sum_{i \in U_2, i \neq k} p_i^{(n)}|w_k^{(n)H} h_i^{cb}|^2 + \sigma_b^2 (k \in U_2)$$

and $$g_c(p_c^{(n)}) = [1 + 1/(2^{2R_{pk}} - 1)] p_c^{(n)}|h_c^{cp}|^2,$$

λ represents an any auxiliary Lagrange factor and $h_c^{cp}$ represents the channel response from the cth cognitive user to the receiver of the primary user. For the cognitive users in the set $U_2$, the power distribution factor $\hat{\alpha}_c^{(m)}=1$ ($c \in U_2$);
4) Judging whether the iteration stopping condition $\|\hat{\alpha}^{(m)} - \hat{\alpha}^{(m-1)}\|/\|\hat{\alpha}^{(m-1)}\| \leq \epsilon$ is met or not, if so, indicating that the power distribution factor vectors obtained in the nth iteration and the (n−1)th iteration hardly change, namely the iteration process converges, then continuously implementing the step 5); and otherwise, repeatedly implementing the step 2);
5) Outputting the final convergent value: $\bar{\alpha}(\lambda) = \hat{\alpha}^{(m)}$.

The value of the auxiliary Lagrange factor λ of the invention is determined according to a bisection search algorithm, and the specific implementation process is as follows:
1) Setting initial values $\lambda^+=0$ and $\lambda^-$ of a bisection search algorithm, wherein $\lambda^+$ is the initial value for realizing $$\sum_{c \in U_1} \bar{\alpha}_c(\lambda^+) g_c(p_c^{(n)}) < C(p^{(n)}),$$

indicating that $\lambda^+$ can enable the cognitive network to provide a greater transmission rate than the target transmission rate of the primary user; and $\lambda^-$ is the initial value for realizing $$\sum_{c \in U_1} \bar{\alpha}_c(\lambda^+) g_c(p_c^{(n)}) > C(p^{(n)}),$$

indicating that $\lambda^-$ can enable the cognitive network to provide a less transmission rate than the target transmission rate of the primary user. Wherein $$C(p^{(n)}) = \frac{1}{2^{2R_{pk}} - 1} \sum_{c \in N_1} p_c^{(n)}|h_c^{cp}|^2 - \sum_{c \in N_2} p_c^{(n)}|h_c^{cp}|^2 - \sigma_p^2, \sigma_p^2$$

is the channel noise power received by the receiver of the primary user, and $R_{pk}$ is the target transmission rate of the primary user. Setting the judging criteria of iteration stopping $\epsilon$, $\epsilon \in [10^{-2}, 10^{-4}]$;
2) Enabling $$\lambda = \frac{\lambda^+ + \lambda^-}{2},$$

and obtaining the power distribution factor vector $\bar{\alpha}(\lambda)$ according to the above iterative calculation process of the power distribution factor;

If $\sum_{c \in N_1} \bar{\alpha}_c(\lambda) g_c(p_c^{(n)}) < C(p^{(n)})$, then $\lambda^- = \lambda$;

If $\sum_{c \in N_1} \bar{\alpha}_c(\lambda) g_c(p_c^{(n)}) > C(p^{(n)})$, then $\lambda^+ = \lambda$;

3) Judging whether the search stopping condition $$\left|\sum_{c \in U_1} \bar{\alpha}_c(\lambda) g_c(p_c^{(n)}) - C(p^{(n)})\right| / C(p^{(n)}) \leq \varepsilon$$

is met or not, if so, indicating that the transmission rate which is provided by the cognitive network for the primary user is basically equivalent to the target transmission rate of the primary user, then continuously implementing the step 4); and otherwise, repeatedly implementing the step 2);
4) Outputting the final result: $\alpha^{(n)} = \bar{\alpha}(\lambda)$.

In the step 4.1 of the invention, $\alpha_c^{(n)} = x$, $c=1, 2, \ldots, N$, wherein x is a decimal and $x \in [0, 1]$.

Compared with the prior art, the invention has the following advantages:

The invention designs the resource distribution method for throughput maximization in the cognitive SIMO network based on the cooperative relay. According to the combined adjustment of the transmission power vector, the power distribution factor vector and the beamforming weight vectors, the maximum throughput performance of the cognitive network can be realized while the target transmission rate of the primary user is ensured, in addition, very fast convergence rate can be realized in the proposed resource distribution method.

DETAILED DESCRIPTION OF THE INVENTION

Figure 1:
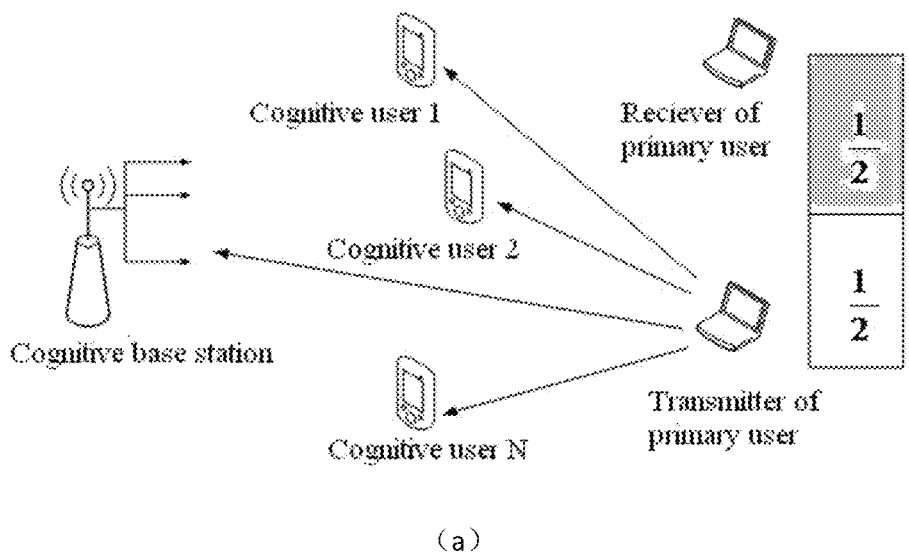
FIG. 1 is a cognitive SIMO network access model based on cooperative relay.
(a) A cognitive SIMO network access model; and
(b) A resource distribution model after the access of the cognitive SIMO network.
Figure 1:
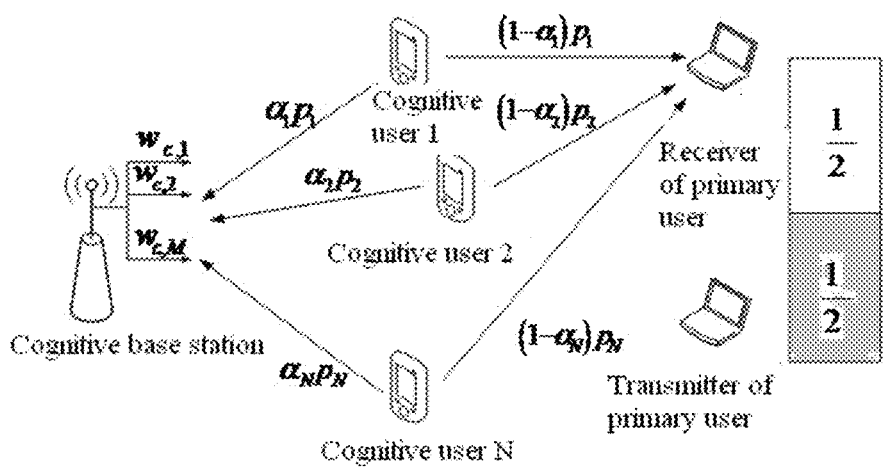

An embodiment of the invention is described as follows: system simulation adopts MatLab simulation, and the setting of parameters does not affect generality. A primary user system comprises a single-antenna transmitter and a single-antenna receiver, and the receiver is randomly distributed on a circumference with a radius of 200 m by taking the transmitter as the center of a circle. A cognitive network comprises a multi-antenna cognitive base station and three single-antenna cognitive users, and the three cognitive users are randomly distributed on the circumference with the radius of 200 m by taking the base station as the center of the circle. A logarithmic path loss model is used for modeling large-scale path loss of the channels, and a loss factor is set as 4; a Rayleigh fading model with mean 1 is used for modeling small-scale fading of the channels; the noise power at the receiver is set as $\sigma_b^2 = \sigma_c^2 = \sigma_p^2 = -110$ dBm; the transmission power of the primary transmitter is 0 dBm; and the three cognitive users have a same peak transmission power $p_{max}$.

The specific process of the embodiment is described by taking a following independent random test as an example. In the random test, the number of antennas of the cognitive base station is set as M=3, the distance between the cognitive base station and the transmitter of the primary user is set as 100 m, the allowable peak transmission power of the three cognitive users is set as $p_{max}=20$ dBm, and the target transmission rate of the primary user is set as $R_{pk}=1$ bps/Hz.

Step 1: the transmitter of the primary user broadcasts a cooperation request message CRM, the receiver of the primary user replies a cooperation acknowledge message CAM. The cognitive base station estimates the channel state information in the network from the received CRM and CAM, then judges whether the cognitive SIMO network has the ability of cooperating with the primary user to achieve the target transmission rate of the primary user or not, if yes, the cognitive base station sends a cooperation confirmation message CCM to the primary user and the cognitive SIMO network is accessible to the frequency band licensed to the primary user; and otherwise, the cognitive SIMO network is non-accessible to the licensed frequency band. In the random test, according to the assumed path loss and path fading models, four groups of the channel responses in the network which are randomly generated by Matlab simulation software are as follows:

1. The channel response vector from the transmitter of the primary user to the cognitive base station: $h^{pb}=[1.1967 \times 10^{-4}, 1.117 \times 10^{-5}, 1.1488 \times 10^{-4}]^T$;

2. The channel responses from the transmitter of the primary user to all the cognitive users: $h_1^{pc}=2.9093 \times 10^{-5}$, $h_2^{pc}=2.6325 \times 10^{-5}$, $h_3^{pc}=1.7732 \times 10^{-5}$;

3. The channel response vectors from all the cognitive users to the cognitive base station: $h_1^{cb}=[3.8387 \times 10^{-5}, 2.0909 \times 10^{-5}, 3.1236 \times 10^{-5}]^T$, $h_2^{cb}=[1.545 \times 10^{-5}, 1.9064 \times 10^{-5}, 9.1956 \times 10^{-7}]^T$, $h_3^{cb}=[5.619 \times 10^{-6}, 3.8369 \times 10^{-5}, 1.7549 \times 10^{-5}]^T$;

4. The channel responses from all the cognitive users to the receiver of the primary user: $h_1^{cp}=1.535 \times 10^{-5}$, $h_2^{cp}=1.8538 \times 10^{-5}$, $h_3^{cp}=1.167 \times 10^{-5}$.

According to the cognitive SIMO network access method based on cooperative relay in the patent number of 201110178680.2, which is provided by the applicant, we can judge that the cognitive SIMO network is accessible to the frequency band licensed to the primary user, and all the three cognitive users and the cognitive base station can successfully decode the data of the primary user, so that the cognitive base station sends the CCM to the primary user.

Step 2: the cognitive network receives the data of the primary user, that comprises:

after the transmitter and the receiver of the primary user receive the CCM, the primary transmitter starts to send its information data, the cognitive network keeps silent and receives the data of the primary user, simultaneously, the cognitive base station and the cognitive users being capable of successfully decoding the data of the primary user decode the data. In the random test, both the cognitive base station and the three cognitive users decode the data of the primary user.

Step 3: the cognitive users send the data of themselves and simultaneously relay the data of the primary user, that comprises:

the cognitive user 1, the cognitive user 2 and the cognitive user 3 which successfully decode the data of the primary user in the step 2 use part of their transmission power $\alpha_1 p_1$, $\alpha_2 p_2$ and $\alpha_3 p_3$ to send the data of themselves to the cognitive base station, and the remaining transmission power $(1-\alpha_1)p_1$, $(1-\alpha_2)p_2$ and $(1-\alpha_3)p_3$ are used for forwarding the data of the primary user to the primary receiver;

Step 4: the cognitive base station eliminates the interference caused by the data of the primary user from the received mixed signals and performs beamforming on the signals after eliminating the interference. According to the combined adjustment of the transmission power vector $p=[p_1, p_2, p_3]^T$, the power distribution factor vector $\alpha=[\alpha_1, \alpha_2, \alpha_3]^T$, and the beamforming weight vectors $w_1$, $w_2$, $w_3$, the maximum throughput can be realized in the cognitive SIMO network on the premise of ensuring the target transmission rate $R_{pk}$ of the primary user.

In the step 4, p, $\alpha$ and $w_1$, $w_2$, $w_3$ are determined according to the following iteration process, that comprises:

Step 4.1 Initializing: n=0, $p_c^{(n)}=20$ dBm (c=1, 2, 3), $\alpha_c^{(n)}=1$(c=1, 2, 3) and $R_{sum}^{(n)}=0$, wherein n represents the number of iterations, $p_c^{(n)}$ and $\alpha_c^{(n)}$ represent the transmission power and the power distribution factor of the cth cognitive user at the nth iteration respectively, and $R_{sum}^{(n)}$ represents the throughput of the cognitive network at the nth iteration. Setting the judging criteria of iteration stopping $\epsilon=0.001$.

Step 4.2 Adding 1 to the number of iterations: n=n+1.

Step 4.3 Fixing the transmission power vector and the power distribution factor vector as $p^{(n-1)}$ and $\alpha^{(n-1)}$ of the (n-1)th iteration and calculating the beamforming weight vectors $w_c^{(n)}$ (c=1, 2, 3) at the nth iteration:

$$w_c^{(n)} = \eta \left( \sum_{i=1, i \neq c}^{3} \alpha_i^{(n-1)} p_i^{(n-1)} h_i^{cbH} h_i^{cb} + \sigma_b^2 I_{N_t} \right)^{-1} h_c^{cb} \qquad (5)$$

Wherein $I_{N_t}$ represents an $N_t \times N_t$ unit matrix and $\eta$ is a scaler factor for normalizing $w_c^{(n)}$.

Step 4.4 Fixing the beamforming weight vectors as $w_c^{(n)}$ (c=1, 2, 3) of the nth iteration, fixing the power distribution factor vector as $\alpha^{(n-1)}$ of the (n−1)th iteration and calculating the transmission power vector $p^{(n)}$ of the nth iteration. $p^{(n)}$ is determined by the following iteration process:

1) Initializing: m=0 and $\hat{p}_c^{(m)}$=0 (c=1, 2, 3), wherein m represents the number of iterations, $\hat{p}_c^{(m)}$ represents the transmission power of the cth cognitive user at the mth iteration. Setting the judging criteria of iteration stopping $\epsilon$=0.001.
2) Adding 1 to the number of iterations: m=m+1
3) Calculating the transmission power vector $\hat{p}_c^{(m)}$ (c=1, 2, 3) at the mth iteration $$\hat{p}_c^{(m)} = \left[ \left( \sum_{k=1, k \neq c}^{3} \frac{\alpha_c^{(n-1)} |w_k^{(n)H} h_c^{cb}|^2}{\sum_{i=1, i \neq k}^{N} \hat{p}_i^{(m-1)} \alpha_i^{(n-1)} |w_k^{(n)H} h_i^{cb}|^2 + \sigma_b^2} \right)^{-1} \right]^{p_{c, max}} \qquad (6)$$

4) Judging whether the stopping condition $\|\hat{p}^{(m)} - \hat{p}^{(m-1)}\|/\|\hat{p}^{(m-1)}\| < \epsilon$ is met or not, if so, continuously implementing the step 5); and otherwise, repeatedly implementing the step 2);
5) Outputting the final convergent value $p^{(n)} = \hat{p}^{(m)}$, wherein $p^{(n)}$ is the transmission power vector of the nth iteration in the step 4.4.

Step 4.5 Fixing the beamforming weight vectors and the transmission power vector as $w_c^{(n)}$ (c=1, 2, 3) and $p^{(n)}$ of the nth iteration, and calculating the power distribution factor vector $\alpha^{(n)}$ of the nth iteration. A non-negative auxiliary variable, namely a Lagrange factor $\lambda$, needs to be introduced in the calculation process of $\alpha^{(n)}$, the $\lambda$ is determined through a bisection search algorithm, and the corresponding $\overline{\alpha}(\lambda)$ needs to be calculated during the process of updating $\lambda$ every time. For any $\lambda \geq 0$, $\overline{\alpha}(\lambda)$ is determined according to the following iteration process:

1) Initializing: m=0 and $\hat{\alpha}_c^{(m)}$=0 (c=1, 2, 3), wherein m represents the number of iterations, and $\hat{\alpha}_c^{(m)}$, represents the power distribution factor of the cth cognitive user at the mth iteration. Setting the judging criteria of iteration stopping $\epsilon$=0.001.
2) Adding 1 to the number of iterations: m=m+1
3) Calculating the power distribution factor of the cth cognitive user at the mth iteration by utilizing the following formula:

$$\hat{\alpha}_c^{(m)} = \left[ \left( \sum_{k=1, k \neq c}^{3} \frac{p_c^{(n)} |w_k^{(n)H} h_c^{cb}|^2}{\sum_{i=1, i \neq k}^{3} \hat{\alpha}_i^{(m-1)} p_i^{(n)} |w_k^{(n)H} h_i^{cb}|^2 + \sigma_b^2} + \lambda g_c(p_c^{(n)}) \right)^{-1} \right]^{1} \qquad (7)$$

wherein $g_c(p_c^{(n)}) = [1 + 1/(2^{2R_{pk}} - 1)] p_c^{(n)} |h_c^{cp}|^2$.

4) Judging whether the stopping condition $\|\hat{\alpha}^{(m)} - \hat{\alpha}^{(m-1)}\|/\|\hat{\alpha}^{(m-1)}\| < \epsilon$ is met or not, if so, continuously implementing the step 5); and otherwise, repeatedly implementing the step 2);
5) Outputting the final convergent value: $\overline{\alpha}(\lambda) = \hat{\alpha}^{(m)}$.

The auxiliary variable $\lambda$ is determined according to the following bisection search algorithm:

1) Setting the initial values $\lambda^+$=0 and $\lambda^-$=$10^7$ of the bisection search algorithm. Wherein $\lambda^+$ represents the initial value for realizing $$\sum_{c=1}^{3} \overline{\alpha}_c(\lambda^+) g_c(p_c^{(n)}) > C(p^{(n)}),$$

$\lambda^-$ represents the initial value for realizing $$\sum_{c=1}^{3} \overline{\alpha}_c(\lambda^-) g_c(p_c^{(n)}) < C(p^{(n)})$$

and $$C(p^{(n)}) = \frac{1}{2^{2R_{pk}} - 1} \sum_{c=1}^{3} p_c^{(n)} |h_c^{cp}|^2 - \sigma_b^2.$$

Setting the judging criteria of iteration stopping $\epsilon$=0.001.
2) Enabling $$\lambda = \frac{\lambda^+ + \lambda^-}{2},$$

and obtaining the power distribution factor vector $\overline{\alpha}(\lambda)$ according to the above calculation process. If $$\sum_{c=1}^{3} \overline{\alpha}_c(\lambda) g_c(p_c^{(n)}) < C(p^{(n)}),$$

then $\lambda^- = \lambda$; and if $$\sum_{c=1}^{3} \overline{\alpha}_c(\lambda) g_c(p_c^{(n)}) > C(p^{(n)}),$$

then $\lambda^+ = \lambda$.
3) Judging whether the stopping condition $$\left| \sum_{c=1}^{3} \overline{\alpha}_c(\lambda) g_c(p_c^{(n)}) - C(p^{(n)}) \right| / C(p^{(n)}) \leq \epsilon$$

is met or not, if so, continuously implementing the step 4); and otherwise, repeatedly implementing the step 2);
4) Outputting the final result $\alpha^{(n)} = \overline{\alpha}(\lambda)$, wherein $\alpha^{(n)}$ is the power distribution factor vector of the nth iteration in the step 4.5.

Step 4.6 Calculating the throughput $R_{sum}^{(n)}$ of the cognitive network after the nth iteration by utilizing the following formula:

$$R_{sum}^{(n)} = \sum_{c=1}^{3} \frac{1}{2} \log \left( 1 + \frac{\alpha_c^{(n)} p_c^{(n)} |w_c^{(n)H} h_c^{cb}|^2}{\sum_{i=1, i \neq c}^{3} \alpha_i^{(n)} p_i^{(n)} |w_c^{(n)H} h_i^{cb}|^2 + \sigma^2} \right) \quad (8)$$

Step 4.7 Judging whether the iteration stopping condition $|R_{sum}^{(n)} - R_{sum}^{(n-1)}|/R_{sum}^{(n-1)} \leq \epsilon$ is met or not, if so, continuously implementing the step 4.8; and otherwise, repeatedly implementing the step 4.2;

Step 4.8 Outputting the final values after convergence: $w_c = w_c^{(n)}$ (c=1, 2, 3), $p = p^{(n)}$, $\alpha = \alpha^{(n)}$ and $R_{sum} = R_{sum}^{(n)}$ According to the above-mentioned steps, in the first iteration in the random test, $w_1^{(1)} = [0.7145, 0.3892, 0.5814]^T$, $w_2^{(1)} = [0.6292, 0.7764, 0.0374]^T$, $w_3^{(1)} = [0.1320, 0.9014, 0.4123]^T$, $p^{(1)} = [0.1, 0.1, 0.1]^T$(W), $\alpha^{(1)} = [0.0031, 0.0109, 0.0046]^T$ and $R_{sum}^{(1)} = 0.2828$ bps/Hz, the iteration stopping condition is not met, and the second iteration is performed.

In the second iteration, $w_1^{(2)} = [0.4928, -0.4172, 0.7636]^T$, $w_2^{(2)} = [0.5021, 0.3088, -0.8078]^T$, $w_3^{(2)} = [-0.6838, 0.5527, 0.4764]^T$, $p^{(2)} = [0.1, 0.1, 0.1]^T$(W), $\alpha^{(2)} = [0.2764, 0.1744, 0.395]^T$ and $R_{sum}^{(2)} = 14.4409$ bps/Hz, the iteration stopping condition is not met, and the third iteration is performed.

In the third iteration, $w_1^{(3)} = [0.4768, -0.4224, 0.7709]^T$, $w_2^{(3)} = [0.4991, 0.2991, -0.8133]^T$, $w_3^{(3)} = [-0.6889, 0.5362, 0.4878]^T$, $p^{(3)} = [0.1, 0.1, 0.1]^T$ (W), $\alpha^{(3)} = [0.2531, 0.1732, 0.4379]^T$ and $R_{sum}^{(3)} = 15.5196$ bps/Hz, the iteration stopping condition is not met, and the fourth iteration is performed.

In the fourth iteration, $w_1^{(4)} = [0.4768, -0.4224, 0.7709]^T$, $w_2^{(4)} = [0.4991, 0.2991, -0.8133]^T$, $w_3^{(4)} = [-0.6889, 0.5362, 0.4878]^T$, $p^{(4)} = [0.1, 0.1, 0.1]^T$(W), $\alpha^{(4)} = [0.2531, 0.1732, 0.4379]^T$ and $R_{sum}^{(4)} = 15.5196$ bps/Hz, the iteration stopping condition is met, the iteration process is stopped, and the following final results are outputted:

$w_1 = [0.4768, -0.4224, 0.7709]^T$, $w_2 = [0.4991, 0.2991, -0.8133]^T$, $w_3 = [-0.6889, 0.5362, 0.4878]^T$ $p = [0.1, 0.1, 0.1]^T$ (W), $\alpha = [0.2531, 0.1732, 0.4379]^T$, $R_{sum} = 15.5196$ bps/Hz. Using the resource distribution method, the rate provided by the cognitive network for the primary user is 1 bps/Hz, which just achieves the target transmission rate of the primary user.

Figure 2:
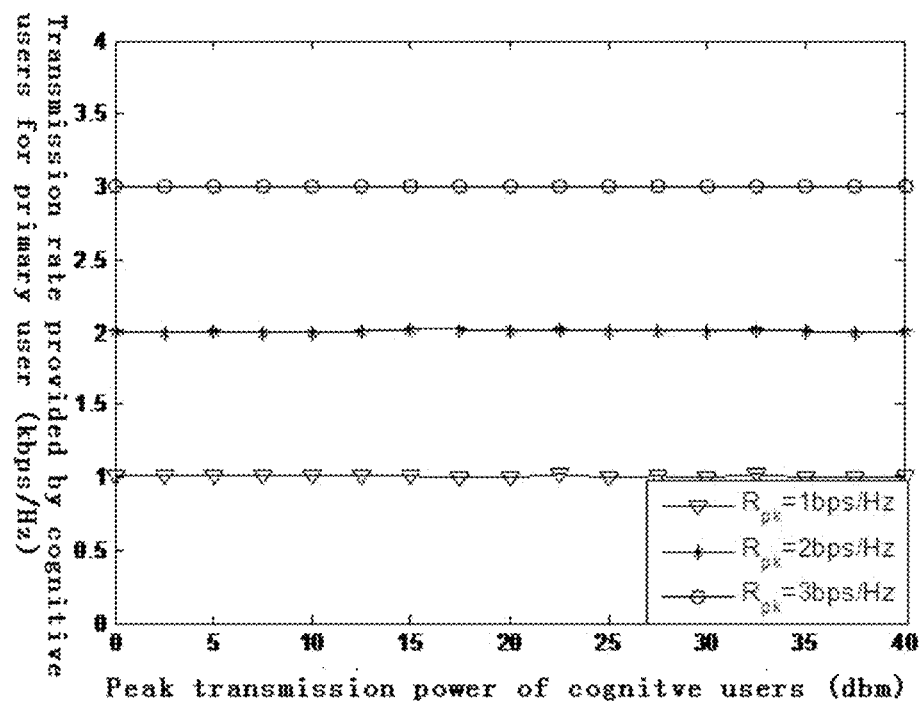
FIG. 2 is a change curve of the data transmission rate provided by the cognitive network for the primary user along with the peak transmission power of the cognitive users according to the resource distribution method of the invention.
Figure 3:
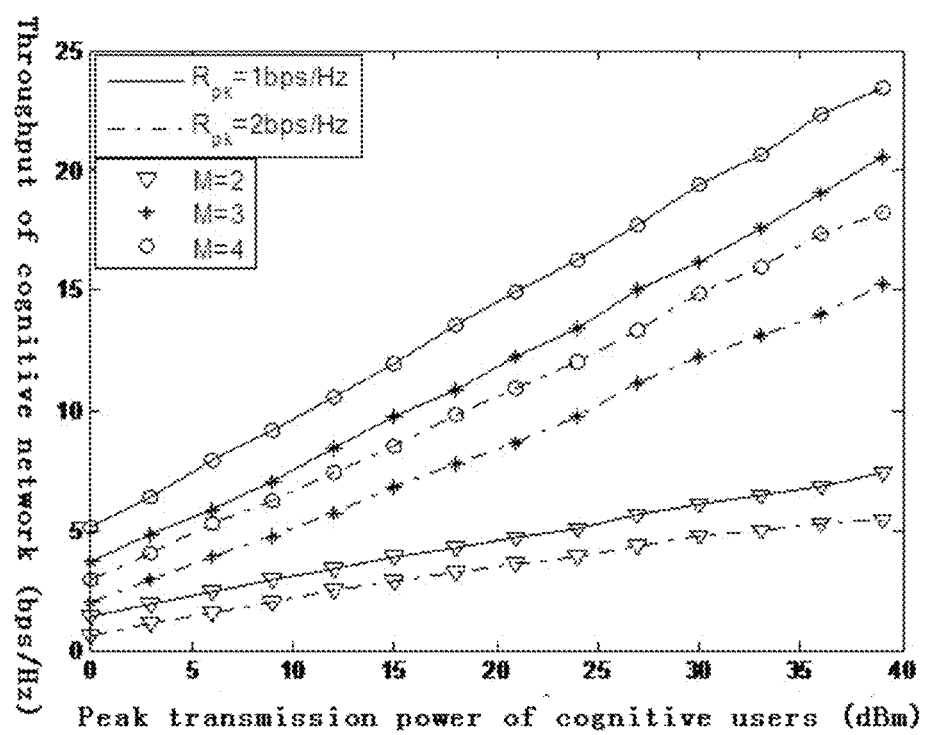
FIG. 3 is a change curve of the achievable network throughput along with the distance between the cognitive network and the primary network according to the resource distribution method of the invention.

The FIG. 2 and FIG. 3 are simulation curves of the invention, and the simulation results are the average values of $10^6$ independent experiments.

The FIG. 2 is a change curve of the transmission rate provided by the cognitive network for the primary user along with the peak transmission power $p_{max}$ of the cognitive users when the target transmission rate of the primary user is $R_{pk} = 1$ bps/Hz, $R_{pk} = 2$ bps/Hz and $R_{pk} = 3$ bps/Hz respectively. The FIG. 2 illustrates that, the resource distribution method of the invention can enable the actual transmission rate of the primary user to just achieve its required target transmission rate regardless of the value of the target transmission rate $R_{pk}$.

The FIG. 3 is a change curve of the throughput of the cognitive SIMO network obtained by the resource distribution method of the invention along with the peak transmission power $p_{max}$ of the cognitive users, and the different target transmission rates $R_{pk}$ and different numbers of the antennas M are considered in simulation. FIG. 3 shows that, along with the increase in the peak transmission power of the cognitive users, the throughput performance of the cooperative cognitive SIMO network is in a linear increase trend, namely the transmission power of the cognitive users is not limited by the primary network, so that the cooperative cognitive SIMO network can realize a large-range network coverage.

Compared with the prior art, the invention has the following advantages:

The invention designs the resource distribution method for throughput maximization in the cognitive SIMO network based on the cooperative relay. According to the combined adjustment of the transmission power vector, the power distribution factor vector and the beamforming weight vectors, the maximum throughput performance of the cognitive network can be realized while the target transmission rate of the primary user is ensured, in addition, very fast convergence rate can be realized in the proposed resource distribution method.

The invention claimed is:

1. A resource distribution method for throughput maximization in a cooperative cognitive SIMO network comprising:

step 1: a transmitter of a primary user broadcasts a cooperation request message (CRM), a receiver of the primary user replies a cooperation acknowledge message (CAM), a cognitive base station estimates channel state information in the cognitive SIMO network from the received CRM and CAM, then judges whether the cognitive SIMO network has ability of cooperating with the primary user to achieve a target transmission rate of the primary user or not, if yes, the cognitive base station sends a cooperation confirmation message (CCM) to the primary user and the cognitive SIMO network being accessible to a frequency band licensed to the primary user; and otherwise, the cognitive SIMO network is non-accessible to the licensed frequency band;

step 2: the cognitive network receives data of the primary user, comprising:

after the transmitter and the receiver of the primary user receive the CCM, the transmitter of the primary user starts to send information data, the cognitive network keeps silent and receives data of the primary user, simultaneously, the cognitive base station and the cognitive users being capable of successfully decoding the data of the primary user decode the data;

step 3: the cognitive users send data of themselves and simultaneously relay the data of the primary user, comprising:

the cognitive users which successfully decode the data of the primary user spend part of their transmission power $\alpha_c p_c$, $c \in U_1$ to send the data of themselves to the cognitive base station, and the remaining transmission power $(1-\alpha_c) p_c$, $c \in U_1$ is spent for forwarding the data of the primary user to the primary receiver; the cognitive users which cannot successfully decode the data do not forward the data of the primary user, all their transmission power $p_c$, $c \in U_2$ is used for sending the data of themselves to the cognitive base station, wherein the set $U_1$ represents a set of the cognitive users being capable of successfully decoding the data of the primary user, a set $U_2$ represents the set of the cognitive users being incapable of successfully decoding the data of the primary user, $p_c$ represents a transmission power of a cth cognitive user and $\alpha_c$ represents a power distribution factor of the cth cognitive user;

step 4: the cognitive base station eliminates the interference caused by the data of the primary user from the received mixed signals and performs beamforming for the signals after eliminating the interference, according to the combined adjustment of a transmission power vector $p = [p_1, p_2, \ldots, p_N]^T$, a power distribution factor vector $\alpha = [\alpha_1, \alpha_2, \ldots, \alpha_N]^T$, $\alpha_c = 1$, $c \in U_2$, and a beamforming weight vectors $w_c = [w_{c,1}, w_{c,2}, \ldots, w_{c,M}]^T$, $c = 1, 2, \ldots, N$, a maximum throughput can be realized in the cognitive SIMO network on a premise of ensuring the target transmission rate of the primary user, wherein M represents a number of antennas configured at the cognitive base station, and N represents a number of the cognitive users in the cognitive network.

2. The resource distribution method for throughput maximization in the cooperative cognitive SIMO network according to claim 1, characterized in that the specific implementation method of the step 4 comprising:

step 4.1 initializing: $n=0$, $p_c^{(n)}=p_{c,max}$, $c=1,2,\ldots,N$, $\alpha_c^{(n)}=x$, $c=1, 2, \ldots, N$ and $R_{sum}^{(n)}=0$, wherein n represents the number of iterations, $p_c^{(n)}$ and $\alpha_c^{(n)}$ represent the transmission power and the power distribution factor of the cth cognitive user at the nth iteration respectively, $p_{c,max}$ represents the peak transmission power allowed by the cth cognitive user, and $R_{sum}^{(n)}$ represents the throughput of the cognitive network at the nth iteration; and setting a judging criterion of iteration stopping $\epsilon$, $\epsilon \in [10^{-2}, 10^{-4}]$;

step 4.2 adding 1 to the number of the iterations: $n=n+1$;

step 4.3 fixing the transmission power vector and the power distribution factor vector as $p^{(n-1)}$ and $\alpha^{(n-1)}$ of the (n−1)th iteration, and enabling the cognitive base station to utilize a maximum SINR beamforming criterion to calculate the beamforming weight vectors $w_c^{(n)}$, $c=1, 2, \ldots, N$ of the nth iteration, wherein the calculation formula is as follows:

$$w_c^{(n)} = \eta \left( \sum_{i=1, i\neq c}^{N} \alpha_i^{(n-1)} p_i^{(n-1)} h_i^{cb} h_i^{cbH} + \sigma_b^2 I_M \right)^{-1} h_c^{cb} \quad (1)$$

wherein $I_M$ represents an M×M unit matrix, $\eta$ is a scaler factor for normalizing $w_c^{(n)}$, and $h_c^{cb}$, $c=1, 2, \ldots, N$ represents an M-dimensional channel vector response from the cth cognitive user to the cognitive base station, $h_i^{cbH}$ is a conjugate of $h_i^{cb}$, and $\sigma_b^2$ represents the channel noise power received by the cognitive base station;

step 4.4 fixing the beamforming weight vectors as $w_c^{(n)}$, $c=1, 2, \ldots, N$ of the nth iteration, fixing the power distribution factor vector as $\alpha^{(n-1)}$ of the (n−1)th iteration and calculating the transmission power vector $p^{(n)}$ of the nth iteration;

step 4.5 fixing the beamforming weight vectors and the transmission power vector as $w_c^{(n)}$, $c=1, 2, \ldots, N$ and $p^{(n)}$ of the nth iteration and calculating the power distribution factor vector $\alpha^{(n)}$ of the nth iteration;

step 4.6 calculating the throughput $R_{sum}^{(n)}$ of the cognitive network after the nth iteration by utilizing the following formula:

$$R_{sum}^{(n)} = \sum_{c=1}^{N} \frac{1}{2} \log \left( 1 + \frac{\alpha_c^{(n)} p_c^{(n)} |w_c^{(n)H} h_c^{cb}|^2}{\sum_{i=1, i\neq c}^{N} \alpha_i^{(n)} p_i^{(n)} |w_c^{(n)H} h_i^{cb}|^2 + \sigma_b^2} \right) \quad (2)$$

step 4.7 judging whether the iteration stopping condition $|R_{sum}^{(n)} - R_{sum}^{(n-1)}|/R_{sum}^{(n-1)} \leq \epsilon$ is met or not, if so, indicating that the throughputs of the cognitive network, which are obtained in the nth iteration and the (n−1)th iteration hardly change, namely the iteration process converges, then continuously implementing the step 4.8; and otherwise, repeatedly implementing the step 4.2;

step 4.8 outputting the final values after convergence: $w_c = w_c^{(n)}$, $c=1, 2, \ldots, N$, $p=p^{(n)}$, $\alpha=\alpha^{(n)}$ and $R_{sum} = R_{sum}^{(n)}$, wherein the throughput $R_{sum}$ of the cognitive network is maximum at this time.

3. The resource distribution method for throughput maximization in the cooperative cognitive SIMO network according to claim 2, characterized in that the calculation process of the transmission power vector $p^{(n)}$ in the step 4.4 at the nth iteration is as follows:

1) initializing: $m=0$ and $\hat{p}_c^{(m)}=0$, $c=1, 2, \ldots, N$, wherein m represents the number of iterations, $\hat{p}_c^{(m)}$ represents the transmission power of the cth cognitive user at the mth iteration, and setting the judging criteria of iteration stopping $\epsilon$, $\epsilon \in [10^{-2}, 10^{-4}]$;

2) adding 1 to the number of iterations: $m=m+1$;

3) calculating the transmission power $\hat{p}_c^{(m)}$, $c=1, 2, \ldots, N$ of the cth cognitive user at the mth iteration by utilizing the following formula;

$$\hat{p}_c^{(m)} = \left[ \left( \sum_{k=1, k\neq c}^{N} \frac{\alpha_c^{(n-1)} |w_k^{(n)H} h_c^{cb}|^2}{\sum_{i=1, i\neq k}^{N} \hat{p}_i^{(m-1)} \alpha_i^{(n-1)} |w_k^{(n)H} h_i^{cb}|^2 + \sigma_b^2} \right)^{-1} \right]^{p_{c,max}} \quad (3)$$

wherein $[b]^{p_{c,max}}$ takes a minimum value of b and $p_{c,max}$;

4) judging whether the iteration stopping condition $\|\hat{p}^{(m)} - \hat{p}^{(m-1)}\|/\|\hat{p}^{(m-1)}\| \leq \epsilon$ is met or not, if so, indicating that the power vectors obtained in the nth iteration and the (n−1)th iteration hardly change, namely the iteration process converges, then continuously implementing the step 5); and otherwise, repeatedly implementing the step 2);

5) outputting the final convergent value: $p^{(n)} = \hat{p}^{(m)}$.

4. The resource distribution method for throughput maximization in the cooperative cognitive SIMO network according to claim 2, characterized in that the calculation process of the power distribution factor vector $\alpha^{(n)}$ in the step 4.5 at the nth iteration comprising:

1) initializing: $m=0$, $\hat{\alpha}_c^{(m)}=0 (c \in U_1)$ and $\hat{\alpha}_c^{(m)}=1 (c \in U_2)$, wherein m represents the number of iterations, $\hat{\alpha}_c^{(m)}$ represents the power distribution factor of the cth cognitive user at the mth iteration; and setting the judging criteria of iteration stopping $\epsilon$, $\epsilon \in [10^{-2}, 10^{-4}]$;

2) adding 1 to the number of iterations: $m=m+1$;

3) calculating the power distribution factor of the $c (c \in U_1)$ th cognitive user at the mth iteration by utilizing the following formula:

$$\hat{\alpha}_c^{(m)} = \left[ \left( \sum_{k \in U_1, k\neq c} \frac{p_c^{(n)} |w_k^{(n)H} h_c^{cb}|^2}{\sum_{i \in U_1, i\neq k} \hat{\alpha}_i^{(m-1)} p_i^{(n)} |w_k^{(n)H} h_i^{cb}|^2 + q_k^1} + \right. \right.$$
$$\sum_{k \in U_2} \frac{p_c^{(n)} |w_k^{(n)H} h_c^{cb}|^2}{\sum_{i \in U_1} \alpha_i^{(m-1)} \hat{p}_i^{(n)} |w_k^{(n)H} h_i^{cb}|^2 + q_k^2} +$$
$$\left. \left. \lambda g_c(p_c^{(n)}) \right)^{-1} \right]^1 \quad (4)$$

wherein $q_k^1 = \sum_{i \in U_2} p_i^{(n)} |w_k^{(n)H} h_i^{cb}|^2 + \sigma_b^2 (k \in U_1)$, $q_k^2 = \sum_{i \in U_2, i\neq k} p_i^{(n)} |w_k^{(n)H} h_i^{cb}|^2 + \sigma_b^2 (k \in U_2)$ and $g_c(p_c^{(n)}) = [1 + 1/(2^{2R_{pk}} - 1)] p_c^{(n)} |h_c^{cp}|^2$, $\lambda$ represents an any auxiliary Lagrange factor and $h_c^{cp}$ represents the channel response from the cth cognitive user to the receiver of the primary user, wherein for the cognitive users in the set $U_2$, the power distribution factor $\hat{\alpha}_c^{(m)}=1(c\in U_2)$;

4) judging whether the iteration stopping condition $\|\hat{\alpha}^{(m)}-\hat{\alpha}^{(m-1)}\|/\|\hat{\alpha}^{(m-1)}\|<\epsilon$ is met or not, if so, indicating that the power distribution factor vectors obtained in the nth iteration and the (n−1)th iteration hardly change, namely the iteration process converges, then continuously implementing the step 5); and otherwise, repeatedly implementing the step 2);

5) outputting the final convergent value: $\overline{\alpha}(\lambda)=\hat{\alpha}^{(m)}$.

5. The resource distribution method for throughput maximization in the cooperative cognitive SIMO network according to claim 4, characterized in that the value of the auxiliary Lagrange factor $\lambda$ is determined according to a bisection search method when the power distribution factor vector $\alpha^{(n)}$ is calculated, and the specific implementation process comprising:

1) setting initial values $\lambda^+=0$ and $\lambda^-$ of a bisection search algorithm, wherein $\lambda^+$ is the initial value for realizing $$\sum_{c\in U_1} \overline{\alpha}_c(\lambda^+)g_c(p_c^{(n)}) > C(p^{(n)}),$$

indicating that $\lambda^+$ can enable the cognitive network to provide a greater transmission rate than the target transmission rate of the primary user; and $\lambda^-$ is the initial value for realizing $$\sum_{c\in U_1} \overline{\alpha}_c(\lambda^+)g_c(p_c^{(n)}) < C(p^{(n)}),$$

indicating that $\lambda^-$ can enable the cognitive network to provide a less transmission rate than the target transmission rate of the primary user, wherein $$C(p^{(n)}) = \frac{1}{2^{2R_{pk}}-1} \sum_{c\in N_1} p_c^{(n)}|h_c^{cp}|^2 - \sum_{c\in N_2} p_c^{(n)}|h_c^{cp}|^2 - \sigma_p^2,$$

is the channel noise power received by the receiver of the primary user, and $R_{pk}$ is the target transmission rate of the primary user; Setting the judging criteria of iteration stopping $\epsilon$, $\epsilon\in[10^{-2}, 10^{-4}]$;

2) enabling $$\lambda = \frac{\lambda^+ + \lambda^-}{2},$$

and obtaining the power distribution factor vector $\overline{\alpha}(\lambda)$ according to the calculation process of the power distribution factor in claim 4;

If $\sum_{c\in N_1} \overline{\alpha}_c(\lambda)g_c(p_c^{(n)}) < C(p^{(n)})$, then $\lambda^- = \lambda$;

If $\sum_{c\in N_1} \overline{\alpha}_c(\lambda)g_c(p_c^{(n)}) > C(p^{(n)})$, then $\lambda^+ = \lambda$;

3) judging whether the search stopping condition $$\left|\sum_{c\in U_1} \overline{\alpha}_c(\lambda)g_c(p_c^{(n)}) - C(p^{(n)})\right| / C(p^{(n)}) \le \varepsilon$$

is met or not, if so, indicating that the transmission rate which is provided by the cognitive network for the primary user is basically equivalent to the target transmission rate of the primary user, then continuously implementing the step 4); and otherwise, repeatedly implementing the step 2);

4) outputting the final result: $\alpha^{(n)}=\overline{\alpha}(\lambda)$.

6. The resource distribution method for throughput maximization in the cooperative cognitive SIMO network according to claim 2, characterized in that, in the step 4.1, $\alpha_c^{(n)}=x$, c=1, 2, ..., N, wherein x is a decimal and $x\in[0,1]$.

* * * * *